United States Patent [19]

Danziger et al.

[11] 4,155,876

[45] May 22, 1979

[54] CATALYST REGENERATION OF BORIC ACID ON CARBON CATALYSTS

[75] Inventors: Harry Danziger; Otto Immel; Bernd-Ulrich Kaiser; Hans-Helmut Schwarz; Klaus Starke, all of Krefeld, Fed. Rep. of Germany

[73] Assignee: Bayer Aktiengesellschaft, Leverkusen, Fed. Rep. of Germany

[21] Appl. No.: 831,936

[22] Filed: Sep. 9, 1977

[30] Foreign Application Priority Data

Sep. 15, 1976 [DE] Fed. Rep. of Germany ....... 2641429

[51] Int. Cl.$^2$ ...................... B01J 21/20; C07D 23/10
[52] U.S. Cl. .................................. 252/417; 252/416; 260/239.3 A
[58] Field of Search ............... 252/416, 417, 419, 432; 260/239.3 A

[56] References Cited

U.S. PATENT DOCUMENTS 3,586,668   6/1971   Immel et al. .................. 260/239.3 A

*Primary Examiner*—Patrick Garvin
*Assistant Examiner*—P. E. Konopka
*Attorney, Agent, or Firm*—Connolly and Hutz

[57] ABSTRACT

A process for the regeneration of a granular, supported catalyst of boric acid on carbon, wherein a part of the catalyst is removed from a fluidized bed reactor, in which cyclohexanone oxime is rearranged into caprolactam on this catalyst, when the "differential content in the catalyst of organic nitrogen" is between 0.3 and 2.0% by weight and is replaced by an equal amount of regenerated catalyst so that the differential organic nitrogen content remains in the above-mentioned range, the quantity of catalyst removed is regenerated with air in a fluidized bed at a temperature of from 400° to 700° C. and is returned to the fluidized bed reactor used for rearrangement when a further part of the catalyst is removed therefrom for regeneration.

2 Claims, No Drawings

CATALYST REGENERATION OF BORIC ACID ON CARBON CATALYSTS

The rearrangement of cyclohexanone oxime into caprolactam in the gaseous phase is carried out inter alia on fixed catalysts of boric acid on combustible supports, for example active carbon or carbon black. Catalysts such as these can be regenerated by oxidation with air at temperatures of 400° to 800° C. However, since the catalysts to be regenerated contain combustible residues, the catalyst supports which are also combustible frequently begin to smoulder, as a result of which crust formation and caking occur.

The object of the present invention is to co-ordinate the use of a catalyst containing boric acid on a carbon support for the rearrangement of cyclohexanone oxime into caprolactam with its regeneration in such a way that the supports do not smoulder during regeneration, the regeneration time remains as short as possible and the energy requirement remains as low as possible.

The present invention relates to a process for regenerating a granular, supported catalyst of boric acid on carbon, wherein a part of, e.g., 5 to 30% by weight of the catalyst is removed from a fluidised bed reactor for the rearrangement of cyclohexanone oxime into caprolactam on this catalyst when the "differential content in the catalyst of organic nitrogen" (as defined below) is between 0.3 and 2.0% by weight and is replaced by an equal amount of regenerated catalyst so that the differential organic nitrogen content remains in the above-mentioned range and the quantity of catalyst removed is regenerated with air in a fluidised bed at a temperature in the range from 400° to 700° C. and is returned to the fluidised-bed rearrangement reactor when a further part of the catalyst is removed therefrom for regeneration.

In the context of this invention, the "differential organic nitrogen content" of the catalyst is the difference in the content of organically bound nitrogen present in the catalyst before and after regeneration expressed in % by weight. Thus, in order to determine the differential organic nitrogen content, the nitrogen content of the catalyst has to be determined before and after regeneration, for example by Kjeldal's method, and the difference calculated therefrom. The nitrogen content of the catalyst increases during the rearrangement of cyclohexanone oxime into caprolactam. According to the invention, this increase in the nitrogen content is used to ascertain the time when it is necessary to regenerate the catalyst. If the nitrogen content increases, part of the catalyst is replaced by regenerated catalyst so that the nitrogen content of the catalyst in the reactor is always maintained within the range 0.3 to 2% by weight above the nitrogen content of the regenerated catalyst. In a given apparatus, the effect of this procedure is that catalyst is removed at regular intervals and replaced by regenerated catalyst. If the rule defined above for the removal of catalyst is adhered to, the boric acid content of the catalyst will also remain constant because during regeneration about as much carbon is burnt as boric acid volatilises from the catalyst during rearrangement. Losses of catalyst through abrasion, discharge and burn-off must of course be made up by fresh catalyst.

Regeneration of the catalyst itself is also simplified. The catalyst generally leaves the rearrangement reactor at a temperature of 300° to 350° C. The regeneration temperature is in the range from 400° to 700° C. and preferably in the range from 550° to 650° C. Accordingly, air may be directly added to the catalyst in a fluidised bed, the temperature rising through burn-up of the carbon. If the temperature rises too quickly, catalyst to be regenerated may be additionally added. If the temperature falls, the input of catalyst may be reduced. Accordingly, regeneration may initially be carried out without any need for the external input or dissipation of energy. It is only after the entire amount of catalyst to be regenerated has been introduced that cooling or heating may have to be applied. The first stage of regeneration generally lasts from 5 to 20 minutes and the second stage 10 to 40 minutes, depending upon the required final activity of the catalyst.

EXAMPLE 150 kg of a 2000 kg batch (= 7.5% by wt.) of a boric acid/carbon black catalyst, which had been used in a fluidised-bed reactor for the rearrangement of cyclohexanone oxime at 330° C. and which had a differential nitrogen content of 1.0%, were passed for 10 minutes through a fluidised-bed regenerator which had been heated to 580° C. with preheated air.

In the meantime, 200 $Nm^3$ of air flowed through the regenerator and established a rate of air flow of about 0.6 m/sec. during regeneration.

On completion of the addition, regeneration was continued for 20 minutes at 600° C., small excess amounts of heat being dissipated by cooling.

After regeneration, the catalyst was introduced first into a catalyst cooler and then into the rearrangement reactor. The regenerated catalyst did not show any signs of caking and was of very high activity.

What we claim is:

1. A process for regenerating a granular supported catalyst of boric acid on carbon containing organically bound nitrogen, said catalyst having been used in the rearrangement of cyclohexanone oxime into caprolactam in a fluidized bed reactor zone, said process comprising removing 5 to 30% by weight of the catalyst from said fluidized bed reactor zone when the differential organic nitrogen content, which is the difference in the content of organically bound nitrogen present in the catalyst before and after regeneration expressed in percent by weight, is between 0.3 and 2.0% by weight, replacing the removed part of said catalyst by an equal amount of regenerated catalyst so that the differential organic nitrogen content is maintained within said range, regenerating the catalyst so removed with air in a fluidized bed at a temperature of from 400° to 700° C. and returning the thusly regenerated catalyst to said fluidized bed reactor zone when a further 5 to 30% by weight of the catalyst is removed therefrom for regeneration.

2. The process of claim 1 wherein regeneration is carried out at a temperature of from 500° to 650° C.

* * * * *